United States Patent
De Lemos et al.

(10) Patent No.: US 8,986,218 B2
(45) Date of Patent: Mar. 24, 2015

(54) SYSTEM AND METHOD FOR CALIBRATING AND NORMALIZING EYE DATA IN EMOTIONAL TESTING

(71) Applicant: iMotions—Eye Tracking APS, Stenlose (DK)

(72) Inventors: Jakob De Lemos, Copenhagen (DK); Ole Baunbaek Jensen, Copenhagen (DK); Golam Reza Sadeghnia, Copenhagen (DK)

(73) Assignee: iMotions A/S, Copenhagen K (DM)

(*) Notice: Subject to any disclaimer, the term of this patent is extended or adjusted under 35 U.S.C. 154(b) by 0 days.

(21) Appl. No.: 13/964,624

(22) Filed: Aug. 12, 2013

(65) Prior Publication Data

US 2013/0331729 A1    Dec. 12, 2013

Related U.S. Application Data

(63) Continuation of application No. 12/170,059, filed on Jul. 9, 2008, now abandoned.

(51) Int. Cl.
*A61B 3/11* (2006.01)
*G06Q 30/02* (2012.01)
*A61B 5/16* (2006.01)
*A61B 3/113* (2006.01)
(Continued)

(52) U.S. Cl.
CPC ............ *A61B 5/165* (2013.01); *A61B 3/112* (2013.01); *A61B 3/113* (2013.01); *A61B 5/1104* (2013.01); *A61B 5/16* (2013.01); *A61B 5/6821* (2013.01)
USPC ........... 600/558; 600/300; 705/7.32; 351/206

(58) Field of Classification Search
USPC ........... 600/300, 558; 351/206–208; 128/898; 705/7.32
See application file for complete search history.

(56) References Cited

U.S. PATENT DOCUMENTS

| | | | |
|---|---|---|---|
| 3,507,988 A | 4/1970 | Holmes | |
| 3,712,716 A | 1/1973 | Cornsweet et al. | 351/7 |

(Continued)

FOREIGN PATENT DOCUMENTS

| | | |
|---|---|---|
| EP | 0 883 049 A1 | 12/1998 |
| JP | H07-313494 | 12/1995 |

(Continued)

OTHER PUBLICATIONS

Bradley, Margaret M. et al. "The pupil as a measure of emotional arousal and autonomic activation." Available online Feb. 12, 2008. Wiley Periodicals, Inc. Psychophysiology, vol. 45. pp. 602-607.*

(Continued)

*Primary Examiner* — Max Hindenburg
*Assistant Examiner* — John Pani
(74) *Attorney, Agent, or Firm* — Pillsbury Winthrop Shaw Pittman LLP

(57) ABSTRACT

A system and method is provided for calibrating and normalizing eye data of one or more subjects prior to and/or during emotional testing of the subjects. In particular, initially performing one or more calibration or normalization operations prior to an emotional test of a subject may result in accurate evaluations of emotional responses based on measurements of eye data. Additionally, further calibration or normalization performed during the emotional test may be used to refine the initial calibration or normalization, further increasing the accuracy of the evaluated emotional responses.

19 Claims, 2 Drawing Sheets

(51) Int. Cl.
*A61B 5/11* (2006.01)
*A61B 5/00* (2006.01)

(56) References Cited

U.S. PATENT DOCUMENTS

| | | | |
|---|---|---|---|
| 3,827,789 A | 8/1974 | Molner et al. ................. 351/23 |
| 3,986,030 A | 10/1976 | Teltscher .................... 250/349 |
| 4,034,401 A | 7/1977 | Mann ............................ 358/93 |
| 4,075,657 A | 2/1978 | Weinblatt ..................... 358/93 |
| 4,146,311 A | 3/1979 | Murr ............................ 351/24 |
| 4,483,681 A | 11/1984 | Weinblatt ................... 434/236 |
| 4,528,989 A | 7/1985 | Weinblatt ................... 128/745 |
| 4,574,314 A | 3/1986 | Weinblatt ................... 358/227 |
| 4,582,403 A | 4/1986 | Weinblatt ................... 351/210 |
| 4,623,230 A | 11/1986 | Weinblatt ................... 351/210 |
| 4,647,964 A | 3/1987 | Weinblatt ..................... 358/84 |
| 4,649,434 A | 3/1987 | Weinblatt ................... 358/250 |
| 4,659,197 A | 4/1987 | Weinblatt ................... 351/210 |
| 4,661,847 A | 4/1987 | Weinblatt ................... 358/108 |
| 4,670,264 A | 6/1987 | Warren et al. ............ 424/195.1 |
| 4,670,463 A | 6/1987 | Warren et al. ................ 514/464 |
| 4,695,879 A | 9/1987 | Weinblatt ..................... 358/84 |
| 4,718,106 A | 1/1988 | Weinblatt ....................... 455/2 |
| 4,837,851 A | 6/1989 | Weinblatt ..................... 455/67 |
| 4,931,865 A | 6/1990 | Scarampi ...................... 358/84 |
| 4,974,010 A | 11/1990 | Cleveland et al. ............ 354/403 |
| 4,992,867 A | 2/1991 | Weinblatt ................... 358/108 |
| 5,090,797 A | 2/1992 | Cleveland et al. ............ 351/210 |
| 5,202,355 A | 4/1993 | Nakatsu ....................... 514/568 |
| 5,204,703 A | 4/1993 | Hutchinson et al. .......... 351/210 |
| 5,219,322 A | 6/1993 | Weathers ....................... 600/27 |
| 5,231,674 A | 7/1993 | Cleveland et al. ................ 382/6 |
| 5,243,517 A | 9/1993 | Schmidt et al. ............. 364/419.2 |
| 5,318,442 A | 6/1994 | Jeffcoat et al. .................. 433/72 |
| 5,380,540 A | 1/1995 | Yamanaka et al. ............ 426/534 |
| 5,406,956 A | 4/1995 | Farwell ....................... 128/731 |
| 5,517,021 A | 5/1996 | Kaufman et al. ............. 250/221 |
| 5,617,855 A | 4/1997 | Waletzky et al. .......... 128/653.1 |
| 5,649,061 A | 7/1997 | Smyth ............................ 395/20 |
| 5,676,138 A | 10/1997 | Zawilinski ................... 128/630 |
| 5,725,472 A | 3/1998 | Weathers ....................... 600/21 |
| 5,884,626 A | 3/1999 | Kuroda et al. ............... 128/630 |
| 5,912,721 A | 6/1999 | Yamaguchi et al. ........... 351/210 |
| 6,021,346 A | 2/2000 | Ryu et al. .................... 600/544 |
| 6,067,842 A | 5/2000 | Gygax et al. ................ 73/23.34 |
| 6,090,051 A | 7/2000 | Marshall ...................... 600/558 |
| 6,102,870 A | 8/2000 | Edwards ...................... 600/558 |
| 6,120,461 A | 9/2000 | Smyth .......................... 600/558 |
| 6,151,571 A | 11/2000 | Pertrushin ................... 704/209 |
| 6,163,281 A | 12/2000 | Torch ............................. 341/21 |
| 6,190,314 B1 | 2/2001 | Ark et al. ..................... 600/300 |
| 6,228,038 B1 | 5/2001 | Claessens .................... 600/558 |
| 6,275,806 B1 | 8/2001 | Pertrushin ................... 704/272 |
| 6,292,688 B1 | 9/2001 | Patton ......................... 600/544 |
| 6,298,263 B1 | 10/2001 | Sedgwick et al. ............. 600/544 |
| 6,346,887 B1 | 2/2002 | Van Orden et al. ........... 340/575 |
| 6,353,810 B1 | 3/2002 | Petrushin .................... 704/236 |
| 6,385,590 B1 | 5/2002 | Levine ........................... 705/10 |
| 6,401,050 B1 | 6/2002 | Cooke et al. ................. 702/127 |
| 6,422,999 B1 | 7/2002 | Hill ............................. 600/300 |
| 6,427,137 B2 | 7/2002 | Petrushin .................... 704/273 |
| 6,429,868 B1 | 8/2002 | Dehner, Jr. et al. ........... 345/440 |
| 6,434,419 B1 | 8/2002 | Gevins et al. ................ 600/544 |
| 6,453,194 B1 | 9/2002 | Hill ............................. 600/546 |
| 6,463,415 B2 | 10/2002 | St. John ....................... 704/273 |
| 6,463,786 B1 | 10/2002 | Behan et al. ................ 73/23.34 |
| 6,480,826 B2 | 11/2002 | Pertrushin ................... 704/270 |
| 6,572,562 B2 | 6/2003 | Marshall ...................... 600/558 |
| 6,585,521 B1 | 7/2003 | Obrador ....................... 434/236 |
| 6,598,971 B2 | 7/2003 | Cleveland .................... 351/209 |
| 6,638,217 B1 | 10/2003 | Liberman .................... 600/300 |
| 6,697,457 B2 | 2/2004 | Petrushin ................... 379/88.08 |
| 6,826,540 B1 | 11/2004 | Plantec et al. .................. 705/10 |
| 6,862,497 B2 | 3/2005 | Kemp et al. ................... 700/264 |
| 6,873,314 B1 | 3/2005 | Campbell .................... 345/156 |
| 6,879,709 B2 | 4/2005 | Tian et al. .................... 382/118 |
| 6,978,243 B2 | 12/2005 | Godinot et al. ................... 705/1 |
| 7,027,621 B1 | 4/2006 | Prokoski ...................... 382/118 |
| 7,110,582 B1 | 9/2006 | Hay ............................ 382/128 |
| 7,113,916 B1 | 9/2006 | Hill ................................ 705/10 |
| 7,120,880 B1 | 10/2006 | Dryer et al. .................. 715/863 |
| 7,155,159 B1 | 12/2006 | Weinblatt et al. ............ 455/2.01 |
| 7,191,403 B2 | 3/2007 | Crain et al. .................. 715/760 |
| 7,246,081 B2 | 7/2007 | Hill ................................ 705/10 |
| 7,302,475 B2 | 11/2007 | Gold et al. ................... 709/217 |
| 7,306,337 B2 | 12/2007 | Ji et al. ....................... 351/209 |
| 7,356,470 B2 | 4/2008 | Roth et al. ................... 704/270 |
| 7,401,920 B1 | 7/2008 | Kranz et al. ................. 351/210 |
| 7,593,952 B2 | 9/2009 | Soll et al. .................... 707/102 |
| 7,657,062 B2 | 2/2010 | Pilu ............................ 382/103 |
| 7,689,499 B1 | 3/2010 | Duquette ....................... 705/37 |
| 7,740,631 B2 | 6/2010 | Bleich et al. .................. 606/79 |
| 7,747,068 B1 | 6/2010 | Smyth et al. ................. 382/154 |
| 7,881,493 B1 | 2/2011 | Edwards et al. .............. 382/103 |
| 8,136,944 B2 | 3/2012 | De Lemos .................... 351/209 |
| 8,814,357 B2 | 8/2014 | De Lemos .................... 351/209 |
| 2002/0007105 A1 | 1/2002 | Prabhu et al. ................... 600/26 |
| 2002/0037533 A1 | 3/2002 | Civelli et al. .................. 435/7.1 |
| 2002/0091654 A1 | 7/2002 | Alroy ............................ 706/21 |
| 2002/0105427 A1 | 8/2002 | Hamamoto et al. ........... 340/576 |
| 2002/0133347 A1 | 9/2002 | Schoneburg et al. .......... 704/257 |
| 2002/0135618 A1 | 9/2002 | Maes et al. ................... 345/767 |
| 2003/0001846 A1 | 1/2003 | Davis et al. .................. 345/474 |
| 2003/0040921 A1 | 2/2003 | Hughes et al. ................... 705/1 |
| 2003/0046401 A1 | 3/2003 | Abbott et al. ................ 709/228 |
| 2003/0078838 A1 | 4/2003 | Szmanda ....................... 705/14 |
| 2003/0123027 A1 | 7/2003 | Amir et al. ................... 351/209 |
| 2003/0125610 A1 | 7/2003 | Sachs et al. .................. 600/300 |
| 2004/0009462 A1 | 1/2004 | McElwrath .................. 434/350 |
| 2004/0044495 A1 | 3/2004 | Lampert et al. .............. 702/127 |
| 2004/0092809 A1 | 5/2004 | DeCharms .................... 600/410 |
| 2004/0098298 A1 | 5/2004 | Yin ................................ 705/10 |
| 2004/0193068 A1 | 9/2004 | Burton et al. ................ 600/544 |
| 2004/0210159 A1 | 10/2004 | Kibar .......................... 600/558 |
| 2004/0249650 A1 | 12/2004 | Freedman et al. ................ 705/1 |
| 2005/0075532 A1 | 4/2005 | Lee et al. ....................... 600/27 |
| 2005/0132290 A1 | 6/2005 | Buchner et al. .............. 715/702 |
| 2005/0175218 A1 | 8/2005 | Vertegaal et al. ............. 382/103 |
| 2005/0221268 A1 | 10/2005 | Chaar et al. .................. 434/350 |
| 2005/0225723 A1 | 10/2005 | Pilu ............................ 351/209 |
| 2005/0228785 A1 | 10/2005 | Wolcott et al. .................. 707/3 |
| 2005/0234779 A1 | 10/2005 | Chiu et al. ..................... 705/24 |
| 2005/0289582 A1 | 12/2005 | Tavares et al. ................. 725/10 |
| 2006/0030907 A1 | 2/2006 | McNew ........................ 607/88 |
| 2006/0049957 A1 | 3/2006 | Surgenor et al. ......... 340/825.19 |
| 2006/0064037 A1 | 3/2006 | Shalon et al. ................ 600/586 |
| 2006/0074742 A1 | 4/2006 | Santandrea .................. 705/10 |
| 2006/0082206 A1 | 4/2006 | Travis ........................ 297/423.1 |
| 2006/0110008 A1 | 5/2006 | Vertegaal et al. ............. 382/103 |
| 2006/0167371 A1 | 7/2006 | Flaherty et al. .............. 600/545 |
| 2006/0167530 A1 | 7/2006 | Flaherty et al. ............... 607/62 |
| 2006/0189900 A1 | 8/2006 | Flaherty ...................... 600/595 |
| 2006/0241356 A1 | 10/2006 | Flaherty ...................... 600/301 |
| 2006/0293948 A1 | 12/2006 | Weinblatt .................... 705/14 |
| 2006/0294537 A1 | 12/2006 | Weinblatt .................... 725/10 |
| 2007/0097234 A1 | 5/2007 | Katayama .................... 348/239 |
| 2007/0097319 A1 | 5/2007 | McKay et al. ................... 353/7 |
| 2007/0100666 A1 | 5/2007 | Stivoric et al. .................. 705/3 |
| 2007/0123794 A1 | 5/2007 | Togino ........................ 600/558 |
| 2007/0150916 A1 | 6/2007 | Begole et al. ................. 725/10 |
| 2007/0167690 A1 | 7/2007 | Miyazaki et al. ............. 600/300 |
| 2007/0260127 A1 | 11/2007 | El-Nokaly et al. ............ 600/301 |
| 2007/0265507 A1* | 11/2007 | de Lemos ................... 600/300 |
| 2007/0273611 A1 | 11/2007 | Torch ............................. 345/8 |
| 2007/0282912 A1 | 12/2007 | Reiner ...................... 707/104.1 |
| 2007/0287881 A1 | 12/2007 | Akimov et al. ................ 600/26 |
| 2007/0300174 A1 | 12/2007 | Macbeth et al. .............. 715/772 |
| 2008/0043013 A1 | 2/2008 | Gruttadauria et al. ......... 345/419 |
| 2008/0065468 A1 | 3/2008 | Berg et al. ..................... 705/10 |
| 2008/0071136 A1 | 3/2008 | Oohashi et al. ................ 600/27 |
| 2008/0146890 A1 | 6/2008 | LeBoeuf et al. .............. 600/300 |
| 2008/0255949 A1 | 10/2008 | Genco et al. ................... 705/14 |
| 2009/0030287 A1 | 1/2009 | Pradeep et al. ............... 600/300 |
| 2009/0270170 A1 | 10/2009 | Patton ........................... 463/36 |

(56) References Cited

U.S. PATENT DOCUMENTS

| | | | |
|---|---|---|---|
| 2010/0004977 A1 | 1/2010 | Marci et al. ................... | 705/10 |
| 2010/0010317 A1 | 1/2010 | De Lemos et al. ............ | 600/300 |
| 2010/0010370 A1 | 1/2010 | De Lemos et al. ............ | 600/558 |
| 2010/0039618 A1 | 2/2010 | De Lemos ................... | 351/209 |
| 2012/0078065 A1 | 3/2012 | De Lemos et al. ............ | 600/301 |
| 2012/0237084 A1 | 9/2012 | De Lemos ................... | 382/103 |

FOREIGN PATENT DOCUMENTS

| | | |
|---|---|---|
| JP | 11014510 | 1/1999 |
| JP | 2000-508557 | 7/2000 |
| JP | 2006-325756 | 12/2006 |
| WO | WO 90/02543 | 3/1990 |
| WO | WO 97/33515 | 9/1997 |
| WO | WO 97/38624 | 10/1997 |
| WO | WO 99/24159 | 5/1999 |
| WO | WO 03/105786 | 12/2003 |
| WO | WO 2005/032503 | 4/2005 |
| WO | WO 2005/043453 | 5/2005 |
| WO | WO 2006/111476 | 10/2006 |
| WO | WO 2007/096706 | 8/2007 |
| WO | WO 2007/102053 | 9/2007 |
| WO | WO 2008/014346 | 1/2008 |
| WO | WO 2008/023260 | 2/2008 |
| WO | WO 2008/129356 | 10/2008 |
| WO | WO 2010/004426 | 1/2010 |
| WO | WO 2010/004429 | 1/2010 |
| WO | WO 2010/018459 | 2/2010 |
| WO | WO 2010/100567 | 10/2010 |

OTHER PUBLICATIONS

Anderson, Keith, "Real-Time Emotion Recognition Using Biologically Inspired Models", Department of Computer Science, Queen Mary College, University of London, [no date], 8 pages.

Brave, Scott, et al., "Emotion in Human-Computer Interaction", Chapter in preparation for *Handbook of Human-Computer Interaction*, Department of Communication, Stanford University, [no date], 50 pages.

Cohn, Jeffrey F., et al., "Multimodal Coordination of Facial Action, Head Rotation, and Eye Motion During Spontaneous Smiles", To appear in *Proceedings of the Sixth IEEE International Conference on Automatic Face and Gesture Recognition (FG'04)*, Seoul, Korea, 7 pages.

Crosby, Martha E., et al., "Physiological Data Feedback for Application in Distance Education", *ACM* 1-58113-448-7-11/14/01, PUI 2001, Orlando, Florida, copyright 2001, 5 pages.

Jackson, Daren C., et al., "Now You Feel It, Now You Don't: Frontal Brain Electrical Asymmetry and Individual Differences in Emotion Regulation", *Physiological Science*, vol. 14, No. 6, Nov. 2003, pp. 612-617.

Jacob, Robert J. K., "Eye Movement-Based Human-Computer Interaction Techniques: Toward Non-Command Interfaces", Human-Computer Interaction Lab, Naval Research Laboratory, Washington, D.C., [no date], 81 pages.

Kulic, D., et al., "Estimating Intent for Human-Robot Interaction" Department of Mechanical Engineering, University of British Columbia, [no date], 6 pages.

Lang, Peter J., "International Affective Picture System (IAPS): Instruction Manual and Affective Ratings", *Technical Report A-6*, The Center for Research in Psychophysiology, University of Florida, 2005, 56 pages.

Papert, Seymour, et al., "Computer Tracking of Eye Motions", *Artificial Intelligence Memo No. 123*, Vision Memo, Massachusetts Institute of Technology, Project MAC, Mar. 1967, 5 pages.

Schafer, Annette, "Companies Spend Billions on Marketing Campaigns, But Neuroscientists Could Someday Determine Which Ads Best Capture Consumers' Attention", *Scientific American Mind*, www.sciammind.com, [no date], pp. 72-75.

Schubert, Emery, "Emotionface: Prototype Facial Expression Display of Emotion in Music", *Proceedings of ICAD 04—Tenth Meeting of the International Conference on Auditory Display*, Sydney, Australia, Jul. 6-9, 2004, 1 page.

Eye Tracking Portal, http://www.eye-tracking.info, three articles: 1) "ASL Launches Mobile Eye", Anonymous, Saturday, Dec. 11 [year?], the URL for this story is http://www.eye-tracking.info/modules.php?name=News&file=article&sid=3, 2 pages. 2) "RIT Takes Eye-Tracking Research to Next Level", Anonymous, Wednesday, Mar. 23 [year?], the URL for this story is http://www.eye-tracking.info/modules.php?name=News&file=article&sid=10, 2 pages. 3) "Did-it, Enquiro, and Eyetools Uncover Google?s Golden Triangle", Anonymous, Mar. 1, 2005, the URL for this story is http://www.eye-tracking.info/modules.php?name=News&file=article&sid=8, 3 pages.

Taylor, J. G., et al., "Modelling the Interaction of Attention and Emotion". *BICS 2004*, Aug. 29-Sep. 1, 2004, Department of Mathematics, King's College, 4 pages.

Tobii Technology, Product Description, Tobii 1750 Eye-Tracker, Release B, Release Date: Nov. 2003, 16 pages.

Tobii Technology, Product Description, ClearView 2, Eye Gaze Analysis Software, Version 2.0, Sep. 2003, 16 pages.

Tobii Technology, Product Description, ClearView 2, Eye-Gaze Analysis Software (describing Release 2.1, Jan. 2004), Copyright 2003, 16 pages.

Bojko, Agnieszka, "Eye Tracking in User Experience Testing: How to Make the Most of It", *Proceedings of the UPA 2005 Conference*, 9 pages.

Yartz, Andrew R., et al., "Addressing the Specificity of Affective Startle Modulation: Fear Versus Disgust", *Biological Psychology*, vol. 59, 2002, pp. 55-68.

Duric et al., "Integrating Perceptual and Cognitive Modeling for Adaptive and Intelligent Human-Computer Interaction", *Proceedings of the IEEE*, vol. 90, No. 7, Jul. 2002, XP011065033, pp. 1272-1289.

Zhai et al., "Realization of Stress Detection Using Psychophysiological Signals for Improvement of Human-Computer Interaction", Southeastcon, 2005, *Proceedings, IEEE*, Ft. Lauderdale, Florida, Apr. 8-10, 2005, XP010789761, pp. 415-420.

Ioannou et al., "Emotion Recognition Through Facial Expression Analysis Based on a Neurofuzzy Network", *Neural Networks*, Elsevier Science Publishers, vol. 18, No. 4, May 2005, XP004965788, pp. 423-435.

Lien et al., "Detection, Tracking, and Classification of Action Units in Facial Expression", *Robotics and Autonomous Systems*, Elsevier Science Publishers, vol. 31, No. 3, May 2000, XP004197692, pp. 131-146.

Ikehara et al., "Assessing Cognitive Load with Physiological Sensors", *Proceedings of the 38th Hawaii International Conference on System Sciences*, Jan. 3, 2005, XP010762783, pp. 295A-1-295A-9.

Partala, Timo et al., "Pupil Size Variation as an Indication of Affective Processing", *International Journal of Human-Computer Studies*, vol. 59, Issues 1-2, Jul. 2003, pp. 185-198.

Nold, Christian, "Bio Mapping", Jan. 2004, www.biomapping.net, 15 pages.

Geirsson, Halldor, "Detection of Outliers", Mar. 21, 2003, hraun.vedur.is/ja/skyrslur/contgps/node1.html, 3 pages.

Alaoui-Ismaili, O. et al., "Odor Hedonics: Connection with Emotional Response Estimated by Automatic Parameters", Oxford University Press, pp. 237-248.

Alata, Mohanad et al., "Text Detection and Character Recognition Using Fuzzy Image Processing", *Journal of Electrical Engineering*, vol. 57, No. 5, 2006, pp. 258-267.

Campbell, Christopher et al., "A Robust Algorithm for Reading Detection", *PUI 2001*, Orlando, Florida, 7 pages.

Goldberg, Joseph et al., "Eye Tracking in Web Search Tasks: Design Implications", ETRA '02, New Orleans, Louisiana, 2002, pp. 51-58.

ISCAN Incorporated, "Magnetic Resonance Remote Eye Tracking Laboratory", Eye & Target Tracking Instrumentation, 2000, 2 pages.

ISCAN Incorporated, "ETL-300 Binocular Free-Head Eye Tracking Laboratory", Eye & Target Tracking Instrumentation, 2000, 4 pages.

ISCAN Incorporated, "ETL-400 Tabletop Remote Eye Tracking Laboratory", Eye & Target Tracking Instrumentation, 2000, 4 pages.

ISCAN Incorporated, "ETL-500 Head-Mounted Eye Tracking Laboratory", Eye & Target Tracking Instrumentation, 2000, 4 pages.

(56) References Cited

OTHER PUBLICATIONS

Niemic, Christopher et al., "Studies of Emotion, A Theoretical and Emperical Review of Psychophysiological Studies of Emotion", jur.rochester.edu, vol. 1, Issue 1, Fall 2002, pp. 15-18.

Pan, Bing et al., "The Determinants of Web Page Viewing Behavior: An Eye-Tracking Study", Association for Computing Machinery, Inc., 2004, pp. 147-154.

Rupp, Heather et al., "Sex Differences in Viewing Sexual Stimuli: An Eye-Tracking Study in Men and Women", *Hormones and Behavior*, vol. 51, 2007, pp. 524-533.

Schnipke, Susan et al., "Trials and Tribulations of Using an Eye-Tracking System", CHI 2000, Apr. 1-6, 2000, pp. 273-274.

Spillers, Frank, Demystifying Usability: Eye-Tracking Studies—Usability Holy Grail?, http://experiencedynamics.blogs.com/site_search_usability/2004/12/eyetracking_stu.html, printed Dec. 7, 2007, 10 pages.

Wilhelm et al., "Affective Computing: Using Computational Intelligence Techniques to Classify the Psychophysiological Signatures of Fearful, Sad, and Calm Affective States", 1 page.

Visual Impact Test—Eye Tracking—Emotional Response—Visual Attention—Eyetracking, Black Box Global Research, printed from http://blackboxglobal.com/visual-impact.html, printed Dec. 7, 2007, 3 pages.

Brave et al., The Human-Computer Interaction Handbook, 2002, pp. 87-88.

Geirsson et al., "Continuous GPS Measurements in Iceland 1999-2002", published Mar. 2003, Chapter 3.2 "Detection of Outliers", 92 pages.

Ebrahimi, Touradj et al., "Brain-Computer Interface in Multimedia Communication", *IEEE Signal Processing Magazine*, Jan. 2003, IEEE Press, USA, pp. 14-24.

Hayashi, Hidehiko, et al., "Eye Movement Tracking to Support the Second Language Learners' Self-Learning in Comprehension of English Texts", *2002 IEEE International Conference on Systems, Man and Cybernetics*, vol. 7, Oct. 9, 2002, XP-002562615, 6 pages.

Brosch, Tobias, et al., "The Perception and Categorisation of Emotional Stimuli: A Review", *Cognition and Emotion*, vol. 24, No. 3, Jan. 1, 2010, pp. 377-400.

Bradley, Margaret M., et al., "The Pupil as a Measure of Emotional Arousal and Autonomic Activation", *Psychophysiology*, vol. 45, available online Feb. 12, 2008, pp. 602-607.

International Search Report and Written Opinion mailed Dec. 16, 2009 in International Application No. PCT/IB2009/006528, 14 pages.

Amendments Under Article 19 filed Feb. 12, 2010 in International Application No. PCT/IB2009/006528, 12 pages.

Reply to Written Opinion filed May 6, 2010 in International Application No. PCT/IB2009/006528, 15 pages.

International Preliminary Report on Patentability mailed Oct. 14, 2010 in International Application No. PCT/IB2009/006528, 12 pages.

Wiley Online Library page for: "The Pupil as a Measure of Emotional Arousal and Automatic Activation", Wiley Online Library, http://onlinelibrary.wiley.com/doi/10.1111/j.1469-8986.2008.00654.x/abstract, available online Dec. 5, 2011, pp. 1-3.

\* cited by examiner

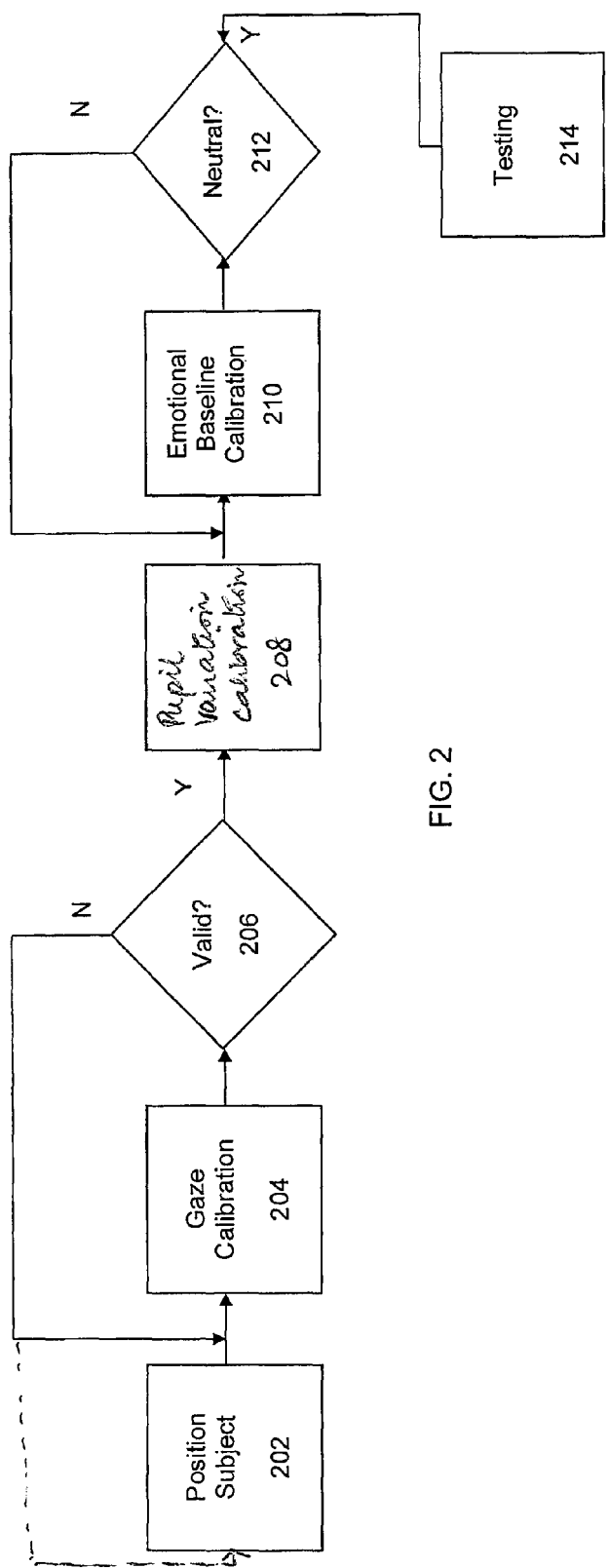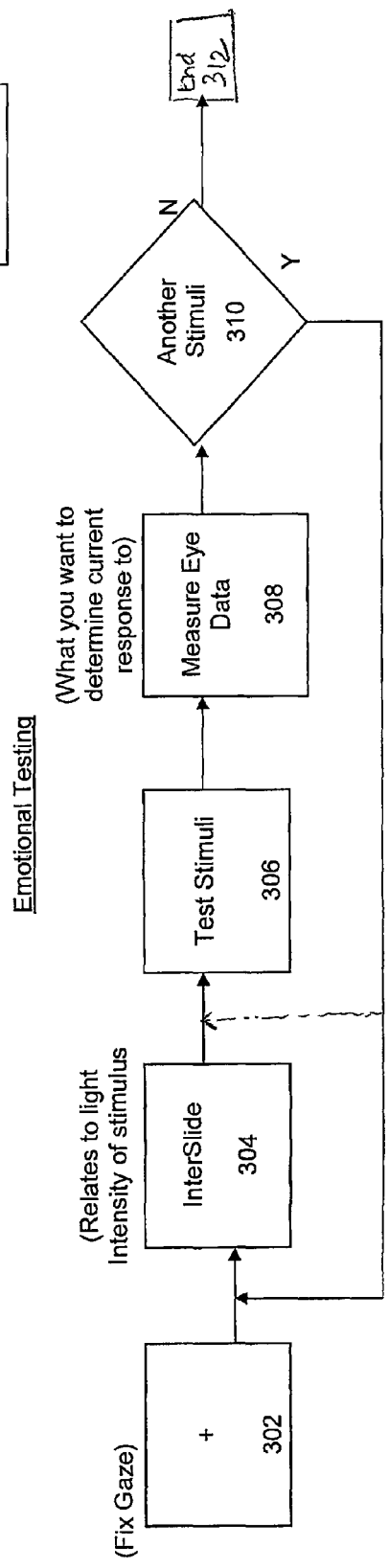

SYSTEM AND METHOD FOR CALIBRATING AND NORMALIZING EYE DATA IN EMOTIONAL TESTING

CROSS-REFERENCE TO RELATED APPLICATIONS

This application is a continuation of U.S. patent application Ser. No. 12/170,059, filed Jul. 9, 2008 (now abandoned), which is hereby incorporated by reference herein in its entirety.

FIELD OF THE INVENTION

The invention relates to calibrating and/or normalizing eye data for one or more subjects prior to, during and/or after emotional response testing based at least on measurements of the eye data for the subjects.

BACKGROUND OF THE INVENTION

In many circumstances, measuring a person's emotional state and/or emotional response to various stimuli may provide valuable information. For example, when marketers, researchers, or other entities desire information relating to emotional responses, various stimuli may be presented to a subject to evaluate an emotional response to the presented stimuli. In general, the stimuli presented to subjects may include a visual stimulus, such as still or moving images, slides, and/or videos. As used herein, a "subject" may generally include, for example, an individual respondent, person, or other test subject for which emotional response data may be desired. In any particular data collection, analysis, or other session testing for emotional responses, subjects may participate actively (e.g., responding to instructions, viewing and responding to various stimuli, etc.) or passively (e.g., collecting data from an unaware subject). As used herein, "emotional response testing" may generally include a variety of activities during one or more test stimuli are presented to a subject to determine the subject's emotional response to the test stimuli (e.g., advertising and/or marketing studies, voter polling, and/or other testing).

Recently, the assignee of the present application has developed a tool referred to as the Emotion Tool™, which provides objective and non-intrusive techniques for evaluating a subject's emotional response and visual attention to stimuli such as print ads, market research materials, brochures, or other stimuli. Some of the techniques for evaluating a subject's emotional response may include measuring and processing various forms of eye data for the subject (e.g., pupil dilation, blink rate, eye movement, etc.). For example, visual stimuli may be presented to the subject on a computer monitor having an eye-tracking device coupled thereto. The eye-tracking device may therefore be used to collect raw eye data from the subject, and the raw eye data may be processed to provide a psycho-physiological interpretation of an emotional response to the presented stimuli. Further details and examples relating to this tool and the techniques used therein can be found in U.S. Patent Application Publication No. 2007/0066916, the disclosure of which is hereby incorporated by reference in its entirety.

Although performing certain calibration steps prior to emotional response testing may generally be known, existing calibration techniques typically focus primarily on gaze tracking (e.g., tracking a location where a subject may be looking at a given moment). Existing techniques for calibrating gaze tracking typically involve presenting a series of indicators at different positions on a monitor (e.g., white circles on a black background), and determining where on the monitor the subject is looking relative to the position of each of the indicators. However, simply calibrating for gaze fails to appreciate that different test subjects can often have different emotional profiles and/or different emotional states at the time of testing (e.g., accurately evaluating a subject's emotional response to a stimulus may depend on whether the subject was happy, angry, confused, or in another emotional state when the test began). Existing techniques that seek to compensate for an initial or preexisting emotional state have focused on attempting to induce a neutral emotional state prior to beginning an emotional response test (e.g., presenting a presumptively neutral slide to the subject to induce the neutral emotional state).

However, these techniques have a limited effect. For example, in some circumstances, merely attempting to induce a neutral emotional state can lead to flawed test results due to differences among test subjects relating to, among other things, emotional profiles, responses to the presumptively emotionally neutral stimuli, ocular physiological characteristics (e.g. pupil size, pupil dilation range, response time, blink characteristics, eye movement characteristics), and/or other differences. For example, where different test stimuli have different light intensity values, various test subjects may experience different physiological responses to the intensity of the stimuli (e.g. pupil dilation may vary from one subject to another). This may be thought of as a light reflex, which is a physical reaction as opposed to an emotional response. In another example, problems can arise because various subjects may look at different portions of a monitor before test stimuli are shown, or worse, subjects may look away from the monitor altogether. These variations, among others, can often lead to errors in the measurement of emotional response.

Existing and known techniques for calibrating and normalizing eye data to be used in emotional response testing suffer from these and other drawbacks.

SUMMARY OF THE INVENTION

Various aspects of the invention overcome these and other drawbacks of prior techniques for emotional testing based on measurements and evaluations of eye data.

According to one implementation of the invention, a calibration phase may be performed prior to emotional testing of one or more subjects to induce a desired emotional state (e.g. an emotionally neutral or other desired state). The desired emotional state may be induced, for example, by presenting certain stimuli to the subject (e.g. a presumptively emotionally neutral stimuli).

Subsequently, an emotional baseline level may be measured for the subject to determine actual characteristics of the subject's emotional state. For example, values for various forms of eye data may be measured to determine whether the subject has reached the desired emotional state (e.g., pupil size, eye movement, blink rate, and/or other eye data). The emotional baseline values may be recorded, providing a set of data that can be used to help ensure that different subjects have a comparable emotional state prior to beginning an emotional response test, and/or to enable use of one or more normalization techniques after testing has begun to determine the subject's actual emotional response to one or more test stimuli.

According to one implementation of the invention, the calibration phase performed prior to the emotional testing may include presenting to the subjects one or more calibration stimuli that have different light intensities (e.g., a zero intensity stimulus, a half intensity stimulus, and a full intensity stimulus). The subject's ocular response to the different light intensities may be measured to determine the subject's light reflex. For example, as the light intensity increases from zero intensity to an intermediate intensity, and then to a full intensity, the range and/or rate of pupil dilation or other forms of eye data may be measured. The measured ocular response information can be used to calibrate and/or normalize the subjects' responses to different test stimuli having different light intensities during testing.

According to one implementation of the invention, one or more conditioning stimuli may be presented to the subject during an emotional testing phase. The conditioning stimuli may include one or more "interslides" (or other forms of stimuli) having predetermined characteristics. The conditioning stimuli may be presented to the subject during various phases of the emotional testing (e.g. between test stimuli). Assuming the emotional testing includes presenting one or more visual test stimuli (e.g. slides), then the conditioning stimuli may be referred to as interslides. If other forms of stimuli are used then other forms of conditioning stimuli may be used. If used, interslides may include one or more slides to neutralize light reflex, for example, to condition a subject between stimuli on which the emotional testing focuses. For example, an interslide conditioning stimulus may have a predetermined light intensity based on a light intensity of a subsequent visual test stimulus. As a result, the interslide conditioning stimulus may condition the subject's eyes to the light intensity of the subsequent test stimulus, such that any ocular response that occurs upon presenting the test stimulus can be based primarily upon the emotional response to the test stimulus, rather than a change in light intensity.

In another example, the conditioning stimuli may include a fixation indicator designed to induce the subject to gaze at a predetermined location of a monitor (e.g., a central point on the monitor, or another point). As such, an eye tracking device may determine whether the subject is looking at the fixation indicator prior to presenting the test stimuli. This can help normalize gaze data by having subjects look at a common point before a test stimuli is presented. This avoids erroneous gaze data readings.

According to one implementation of the invention, various normalization techniques may be used to account for different emotional baseline values, different response profiles to light intensity, and/or other variations among test subjects. These and other techniques may be used together, individually, or in various combinations thereof. For example, a fixation indicator may also be used in combination with sequential variations in light intensity in order to calibrate for both gaze and pupil size/dilation range.

In another example, the calibration and normalization techniques may be used to account for variations in environment that impact emotional responses of test subjects (e.g. from one test to another, at different test sites, etc.). For instance, an identical emotional response test may be presented to a plurality of subjects at a first test site and a second test site, and based on the measurements of the baseline values during the calibration phases, a determination can be made as to whether the first test site or the second test site induces certain emotional states in the test subjects.

According to one implementation of the invention, a system for calibrating and normalizing eye data of one or more subjects may operate in a calibration phase, a test phase, and/or other phase. During the calibration phase, the system may lead the subject through a gaze calibration process, which includes collecting gaze data using an eye-tracking device. The collected gaze data may then be analyzed to determine a validity of the collected gaze data. For example, the collected gaze data may be determined as valid when the subject at least generally looks at certain locations on a monitor that correspond to fixation indicators (e.g., a cross or other indicator to draw the subject's attention). However, when the gaze data appears to be invalid (e.g., because the subject was not looking at the monitor or not looking at the fixation indicators), the gaze calibration may be repeated or other action may be taken, such as prompting the subject to look at the fixation indicators. Upon collecting valid gaze data, the calibration phase may include a short pause prior to a subsequent calibration process that calibrates for emotional baseline, ocular physiological measurement, and/or other forms of eye date. It will also be apparent the calibration phase may proceed directly to the subsequent calibration processes without having the short pause.

According to one implementation of the invention, if desired, the system may cause the monitor to display a fixation indicator to draw the subject's attention to a particular location when the gaze calibration has completed. A light intensity response calibration process may then be implemented to measure eye dilation, pupil dilation size, or another ocular response to changes in light intensity. Various visual stimuli having different light intensity values may be displayed on the monitor at the location where the fixation indicator was presented. For example, a slide or other visual stimuli having a first light intensity may be presented (e.g. a zero intensity or black slide), where the fixation indicator may be shown in connection with the zero intensity slide if desired (e.g. a white cross may be presented on the otherwise black slide). Next, a slide having an intermediate light intensity may be presented followed by another zero intensity slide (e.g. a half intensity or grey slide may be presented prior to another a zero intensity or black slide). Then, the system may show another slide having a full light intensity (e.g. a white slide). In one implementation, the zero intensity and intermediate intensity stimuli may be presented multiple times to gain greater accuracy relating to the variations in the subjects' pupil diameter, while the full intensity stimulus need be shown only once because the full light intensity may not evoke as great a variance in pupil diameter response due to light reflex. The subjects' maximum and minimum pupil diameter may be measured for the zero and intermediate intensity stimuli, and an average pupil diameter may be computed using the maximum pupil diameter following the zero intensity stimuli and the maximum pupil diameter following the intermediate intensity stimuli. When the light intensity calibration has completed, another slide or stimulus may be presented to induce a desired emotional state in the subject to be tested (e.g. a half intensity or grey slide may be presented to induce an emotionally neutral state). Various eye data may then be measured to ensure that the subject has reached the desired emotional state, and one or more of the calibration processes may be repeated until the desired emotional state has been reached.

According to one implementation of the invention, during the test phase, the system may present various test stimuli on the monitor to measure the subject's emotional response. The eye data measured during the calibration phase may therefore be used to normalize the measurements taken during the test phase. For example, where the calibration phase shows that the subject was in a confused state prior to the test phase, a confused response to a given test stimulus may not necessarily indicate that the test stimulus caused the confusion. In another example, when the calibration phase shows that the subject was in an unhappy state prior to the test phase, a pleasurable response to a given test stimulus may indicate that the test stimulus was particularly effective in inducing pleasure in the subject. Additionally and/or alternatively, various interslides or conditioning stimuli may be used during the test phase to reduce variations from one subject to another. For example, when a given test stimulus induces a significant emotional response in a subject, the conditioning stimuli may induce a more neutral state in the subject to ensure that any subsequent response does not carry the effect of the prior stimulus. This may be used, for example, to establish uniform (or other desired) test conditions. Other examples and techniques for using the calibration and conditioning stimuli will be apparent.

According to one implementation of the invention, the system for calibrating and normalizing eye data may include one or more output devices for presenting calibration, test, conditioning, and other stimuli, one or more input devices for collecting eye data, one or more processing devices for analyzing the collected eye data, and one or more data repositories for storing the collected and analyzed eye data.

According to one implementation of the invention, the input devices may include one or more of an eye-tracking device, a manual input device, a sensor, a microphone, a touch-screen display, and/or other input devices to receive input, including eye data, from one or more subjects. The eye-tracking device may include a camera and/or another known eye-tracking device that can record and track various properties of a subject's eyes (e.g., pupil size, blink rate, eye position or gaze, eye movement, etc.). The eye-tracking device may be coupled to a display device, integrated with the display device, and/or configured as a stand-alone device.

According to one implementation of the invention, the eye-tracking device may interface with the processing devices via any suitable wired or wireless connection (e.g., a USB link), and the processing devices may further interface with the output devices that present the calibration stimuli, testing stimuli, conditioning stimuli, and/or stimuli to the subject. The processing devices may therefore include one or more applications to enable the various features and functions of the invention, including one or more modules to perform functions relating to presenting stimuli and analyzing the subject's responses thereto. Non-limiting examples of such modules may include one or more of a calibration module, a stimuli presentation module, a data collection module, a data analysis module, an output module, and/or other modules. The calibration module may comprise one or more of a gaze calibration module, a pupil variation calibration module, an emotional baseline calibration module, an interslide calibration module, and/or other calibration modules. Furthermore, it will be apparent that one or more of the modules comprising the applications may be combined, and that for some purposes, all of the modules may or may not be necessary. The system may be combined with a survey module, facial expression analysis system and modules, behavioral determination systems, cognitive determination systems and/or other physiological measurements.

According to one implementation of the invention, the calibration module may perform one or more calibration steps during a calibration phase, prior to emotional testing of subjects, as described in greater detail above. More particularly, the calibration module may generally include the gaze calibration module to determine whether a subject was looking at an appropriate output device or an appropriate location on the output device. Further, also as described above, the calibration module may include the pupil variation calibration module to determine a subject's pupil diameter and pupil response to differing light intensities. For example, the pupil variation calibration module may sample a pupil size of one or more subjects at different light intensities to detect variations, the absolute values, or ranges in the subjects' pupil diameter in response to the different light intensities.

According to one implementation of the invention, the results of the sampling that the pupil variation calibration module performs may be stored in the data repositories for use during an emotional testing phase. Because pupil diameter variations due to light intensity of various test stimuli may impact the accuracy of eye data collected in response to presenting the test stimuli, the pupil diameter variations may have to be removed from the collected eye data to obtain eye data that corresponds only to the subject's emotional response to the presented test stimuli. For example, as described above, an average pupil diameter of the subject may be computed and used as a scaling factor to remove pupil diameter variations due to light intensity. In particular, pupil data collected during the calibration phase may be used to normalize pupil data relating to the subject's response to different stimuli presented during emotional testing. For example, when the calibration phase results in a determination that the subject has a given average pupil diameter when presented with a stimulus having a certain light intensity, that average pupil diameter may form the scaling factor for test stimuli having comparable light intensities (e.g., the average pupil diameter may be subtracted from the pupil diameter measured in response to the test stimulus, yielding a change in pupil diameter that corresponds only to the subject's emotional response to the test stimulus).

According to one implementation of the invention, the calibration module may include the emotional baseline calibration module to adjust or otherwise condition a subject's emotional level. In particular, prior to emotional testing, the emotional baseline calibration module may attempt to induce an emotional state in the subject that is as close as possible to a desired emotional state (e.g., an emotionally neutral and/or other desired state). For example, the emotional baseline calibration module may present a series of emotionally neutral stimuli to the subject via the output devices until a blink rate pattern, a pupil response, a saccadic, movements, and/or other eye properties reach a desired level. Any given emotionally neutral stimulus or combination of emotionally neutral stimuli related to any of the body's five senses may be presented to the subject. For example, in one implementation, a soothing voice may address the subject to place the subject in a relaxed state of mind. Further, the soothing voice or another emotionally neural stimulus may or may not be accompanied one or more visually pleasant emotionally neutral stimuli and/or other stimuli.

According to one implementation of the invention, the calibration module may include the interslide calibration module to calibrate and/or condition subjects prior to and/or during an emotional test (e.g., the interslide calibration module may present emotionally neutral interslide stimuli to a subject in between or among test stimuli). For example, the interslide calibration module may create the interslide stimuli to have a light intensity identical to a subsequent stimulus that will actually be used in the test. In another example, the interslide calibration module may create the interslide stimuli to have a pixel representation used in the actual test stimulus (e.g., pixel values to be used in the actual test stimulus may be scrambled to create the interslide calibration stimulus with a distinct image yet the same overall light intensity). If non visual stimuli are used (e.g. aroma), the conditioning stimuli may be aromatically neutral (e.g. pure air) or other aroma-based conditioning.

Various other objects, features, and advantages of the invention will be apparent through the detailed description of the implementations and drawings attached hereto. It will also be understood that both the foregoing general description and the following detailed description are exemplary and not restrictive of the scope of the invention.

BRIEF DESCRIPTION OF THE DRAWINGS

FIG. 2 illustrates an exemplary method for performing calibration of one or more subjects prior to emotional testing of the subjects, according to one aspect of the invention.

FIG. 3 illustrates an exemplary method for performing calibration of one or more subjects during emotional testing of the subjects, according to one aspect of the invention.

DETAILED DESCRIPTION

Figure 1:
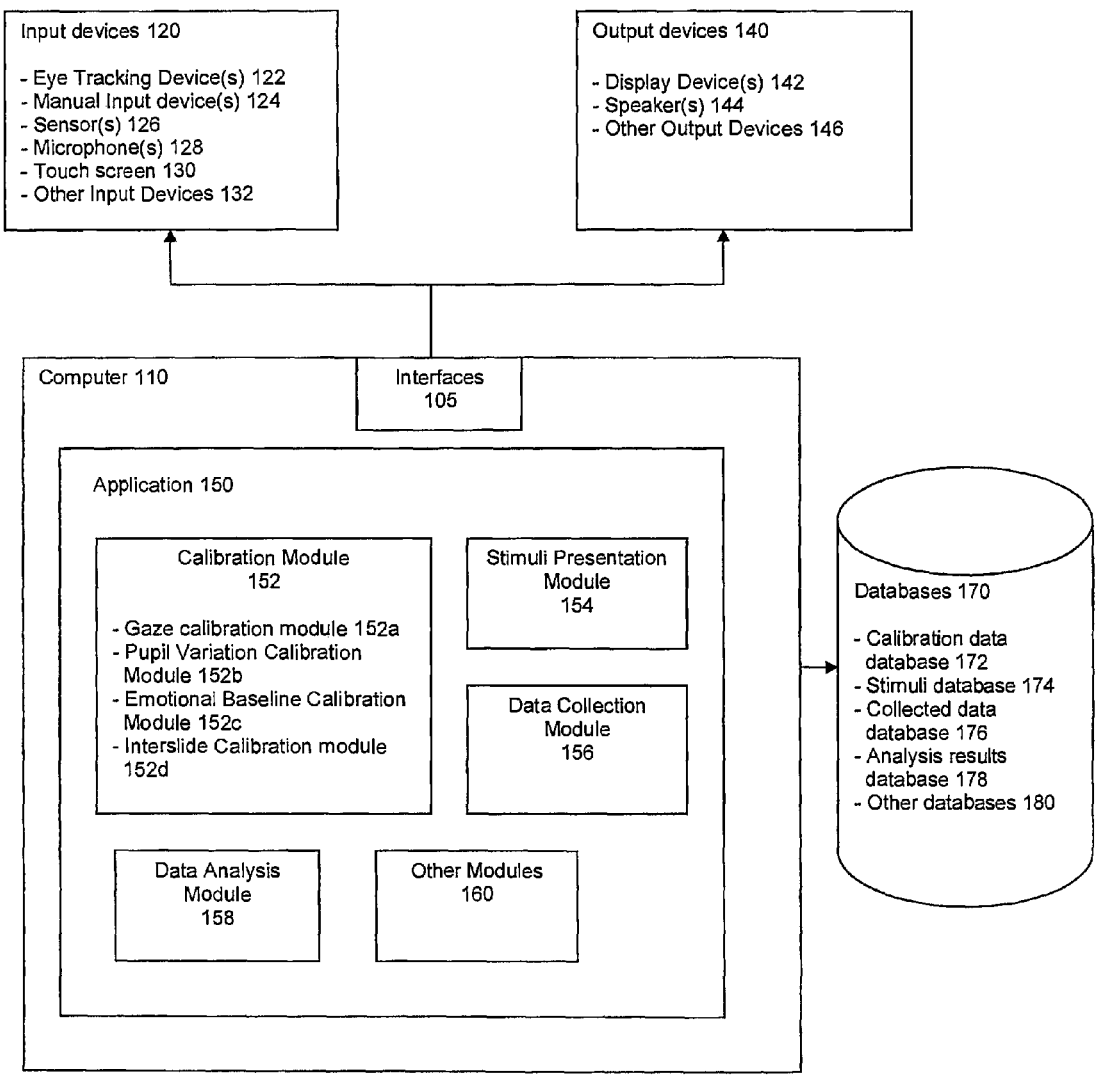
FIG. 1 illustrates an exemplary system for performing calibration of one or more subjects prior to and during emotional testing of the subjects, according to one aspect of the invention.

FIG. 1 illustrates an exemplary system 100 for performing calibration of one or more subjects prior to and during emotional testing of the subjects according to one implementation of the invention. As shown, the system 100 may comprise various components to implement various aspects of the invention, and may be configured to perform various calibration steps prior to and/or during emotional testing of one or more subjects.

The system 100 may include at least one of a computer 110, one or more input devices 120 for collecting eye data, one or more output devices 140 for presenting information to the subjects, and one or more data repositories 170 for storing collected and analyzed eye data. The computer 110 may be operatively coupled to the input devices 120, the output devices 140, and the data repository 170 via one or more interfaces 105.

The one or more input devices 120 may comprise one or more of an eye-tracking device 122, a manual input device 124, a sensor 126, a microphone 128, a touch-screen display 130, and/or other input devices 132 to receive input, including eye data, from one or more subjects. The eye-tracking device 122 may include a camera and/or another known eye-tracking device that can record and track various properties of a subject's eyes (e.g., pupil size, blink rate, eye position or gaze, eye movement, etc.).

The eye-tracking device 122 may be coupled to a display device 142, integrated with the display device 142, and/or configured as a stand-alone device. The manual input device 124 may include one or more of a keyboard, a mouse, and/or another input device that subjects can use to manually input information. The sensors 126 may include one or more emotion detection sensors and/or other sensors. The emotion detection sensors may comprise, for example, one or more physiological sensors such as galvanic skin response sensors, facial recognition sensors, and/or other sensors that can detect various physiological responses from subjects. The subjects may use the microphone 128 to provide voice-based inputs (e.g. when providing a verbal response to various instructions, stimuli, and/or other information).

The touch-screen display 130 may be provided to accept manual input from subjects (e.g., physical contact or pressure applied to a screen via the subjects' finger, a stylus, and/or another body part and/or apparatus). Additionally, in one implementation, the display device 142 may comprise a touch-screen display that can be used to accept manual input in addition to presenting instructions, stimuli, and/or other information to the subjects.

According to one implementation, the one or more output devices 140 may include one or more of the display device 142, a speaker 144, and/or another output devices 146. The display device 142 may comprise one or more monitors, such as a cathode ray tube display, a digital flat panel display, a liquid crystal display, a plasma display, and/or any other display device suitable for presenting instructions, messages, visual stimuli, and/or other information to subjects. The speaker 144 may comprise one or more speakers for audibly reproducing audio instructions or messages, audible stimuli, and/or other information to subjects.

According to one implementation, the one or more databases 170 may be operatively connected to computer 110, and may include and/or interface with one or more databases and/or other resources for storing various types of data. According to one implementation of the invention, the databases 170 may include a calibration database 172, a stimuli database 174, a collected data database 176, an analysis results database 178, and/or other databases 180.

The calibration database 172 may store information relating to one or more calibration stimuli for presentation to subjects prior to and/or during emotional testing of the subjects. The calibration stimuli may comprise one or more stimuli to induce an emotionally neutral state, vary a light intensity, fixate a gaze, or calibrate other eye properties of a subject. The calibration database 172 may also store one or more conditioning stimuli that may be presented to subjects during emotional testing of the subjects (e.g., as "interslides" in between and among test slides).

The stimuli database 174 may store information relating to one or more test stimuli for presentation to subjects during emotional testing of the subjects. As previously noted, the test stimulus or stimuli presented to subjects may comprise any stimulus or combination of stimuli relating to one or more of the subject's five senses (i.e., sight, sound, smell, taste, and touch). The stimulus may comprise any real, analog, or electronic stimulus that can be presented to the subject via known or future-developed technology. Examples of visual stimuli can include, but are not limited to, pictures, artwork, charts, graphs, text, movies, multimedia or interactive content (e.g., video games), and/or other stimuli having visual characteristics. Other types of stimuli may be also be presented to the subjects, either together with or separately from the visual stimulus. The stimuli may be stored on any suitable storage media, and can include live scenarios, textual stimuli (e.g., surveys or questionnaires), olfactory stimuli (e.g., aromas), audible stimuli (e.g., music, recorded voices, sound accompanying a commercial, etc.), or any other suitable stimulus for which an emotional response test may be desired.

The collected data database 176 may store information relating to various forms of eye data (e.g., pupil dilation, blink rate, eye movement, eye position, and/or other eye properties). The computer 110 may acquire the eye data from the eye-tracking device 122 or another of input devices 120. The collected eye data may generally relate to physiological conditions of subjects (e.g., acquired from emotion detection sensors), which has been collected from the subjects during the various calibration, conditioning, normalization, and testing phases described herein. The computer 110 may analyze the data in the collected data database 176 to determine emotional responses of the subjects to calibration, conditioning, test, or other stimuli. Results of analyzing that data may then be stored in the analysis results database 178.

According to one implementation of the invention, the computer 110 may include one or more applications 150 to enable the various features and functions of the invention, including a stimuli presentation module 154 to present stimuli to a subject via the output devices 140, a data collection module 156 to collect eye data and other information from the input devices 120, and a data analysis module 158 to analyze the data collected from the subject in response to the presented stimuli. In addition, a calibration module 152 can be used to calibrate, condition, and otherwise normalize eye data prior to and/or during emotional response testing of the subject. The calibration module 152 may comprise one or more of a gaze calibration module 152a, a pupil variation calibration module 152b, an emotional baseline calibration module 152c, an interslide calibration module 152d, and/or other calibration modules. Furthermore, it will be apparent that one or more of the modules comprising the applications may be combined, and that for some purposes, all of the modules may or may not be necessary.

The calibration module 152 may perform one or more calibration steps during a calibration phase, prior to emotional testing of subjects. In particular, the calibration module 152 may perform one or more calibration steps prior to emotional testing of subjects, including one or more of a gaze fixation calibration, a pupil variation calibration, and an emotional baseline calibration. Additionally, the calibration module 152 may perform one or more interslide or conditioning calibration steps during the emotional testing of subjects.

More particularly, the calibration module 152 may include the gaze calibration module 152a to determine whether a subject was looking at an appropriate output device 140 or an appropriate location on the output devices 140. The gaze calibration module 152a perform a gaze calibration process, which may include instructing a subject to track, with his or her eyes, movement of a visual indicator displayed on display device 142. For example, the visual indicator may assume various shapes, sizes, and/or colors (e.g., a small white cross displayed against a black background). The eye tracking device 122 may then track the subject's gaze as a location on the display device 142 where the subject is currently looking (e.g., x, y, z co-ordinates defining a display position). The calibration module 152 may therefore use the gaze calibration module 152a to establish a frame of reference for the subject's gaze.

In particular, during the gaze calibration process, the data collection module 156 may collect gaze data via the eye-tracking device 122 (e.g., a location on the output devices 140 where the subject may be looking). The data analysis module 158 may then analyze the collected gaze data to determine whether the gaze data is valid (e.g., the gaze data may be rendered invalid upon determining that the subject was not looking at the display device 142). When the gaze data has been determined to be invalid, the gaze calibration module 152a may repeat the gaze calibration process until valid gaze data can be obtained. When repeating the gaze calibration process, the gaze calibration module 152a may instruct the subject to reposition themselves relative to one or more of the output tests 140, and further to track the movement of the visual indicator on the display device 142. In one implementation, the test for the subject may be terminated when the gaze data (from the eye tracker) is invalid.

For example, various data processing techniques can be used to determine if there is noise in the signal. Additionally, if the gaze coordinate(s) is (are) outside a predetermined desired range, the gaze data can be considered invalid. If there is no reaction and/or no change in data over a predetermined period, this may be determined to be invalid data. Other criteria may be used.

According to one implementation, the calibration module 152 may include the pupil variation calibration module 152b to determine a subject's average pupil diameter, response to differing light intensities (e.g. light reflex), or other pupil variations. For example, the pupil variation calibration module may sample a pupil size for one or more subjects at different light intensities to detect variations, the absolute values, or ranges in the subjects' pupil diameter in response to the different light intensities. To enable compensation for these differences, the pupil variation calibration module 152b may be used to calculate pupil diameter variations due to light intensity of various test stimuli. For example, pupil variation calibration module 152b may present one or more emotionally neutral light intensity stimuli of different light intensities (e.g., zero intensity, intermediate intensity, full intensity) to subjects via the display device 142. The eye-tracking device 122 may measure various eye properties of the subjects at the different light intensities (e.g., pupil size, pupil dilation, blink rate, and/or other properties).

Pupil variation calibration module 152b may sample the pupil size of the subject at the different light intensities to detect variations in the subject's pupil diameter in response to the light intensity stimuli of different light intensities. The absolute values of the subject's pupil diameter at different light intensities may be measured, as well as the ranges of the subject's pupil diameter across the different light intensities. To gain better accuracy in determining variations in the subject's pupil diameter, the pupil variation calibration module 152b may present the zero intensity and the intermediate intensity stimuli in a predetermined sequence. In one implementation, the full intensity stimulus may only be shown once because the full intensity does not evoke a great variance in pupil diameter response. Pupil variation calibration module 152b may measure the subject's maximum and minimum pupil diameter for the zero intensity light stimuli and the half intensity light stimuli presented during the predetermined sequence. The pupil variation calibration module 152b may then compute the average pupil diameter as the average of the maximum pupil diameter for the zero intensity stimuli and the maximum pupil diameter for the intermediate intensity stimuli.

According to one implementation of the invention, the calibration module 152 may include the emotional baseline calibration module 152c to adjust or otherwise condition a subject's emotional level. In particular, prior to emotional testing, the emotional baseline calibration module 152c may attempt to induce an emotional state in the subject that is as close as possible to a desired emotional state (e.g., an emotionally neutral and/or other desired state). For example, the emotional baseline calibration module 152c may present a series of emotionally neutral stimuli to the subject via the output devices 140 until a blink rate pattern, a pupil response, a saccadic movement, and/or other eye properties reach a desired level. Any given emotionally neutral stimulus or combination of emotionally neutral stimuli related to any of the body's five senses may be presented to the subject. For example, in one implementation, a soothing voice may address the subject to place the subject in a relaxed state of mind. Further, the soothing voice or another emotionally neural stimulus may or may not be accompanied one or more visually pleasant emotionally neutral stimuli and/or other stimuli, which may or may not include emotionally neutral stimuli.

According to one implementation of the invention, the calibration module 152 may include the interslide calibration module 152d to calibrate and/or condition subjects prior to and/or during an emotional test (e.g., the interslide calibration module 152d may present emotionally neutral interslide stimuli to a subject in between or among test stimuli). For example, the interslide calibration module 152d may create the interslide stimuli to have a light intensity identical to a subsequent stimulus that will actually be used in the test. In another example, the interslide calibration module 152d may create the interslide stimuli to have a pixel representation used in the actual test stimulus (e.g., pixel values to be used in the actual test stimulus may be scrambled to create the interslide calibration stimulus with a distinct image yet the same overall light intensity).

Stimuli presentation module 154 may be used to present to a subject one or more calibration stimuli during a calibration phase, one or more conditioning stimuli during a conditioning calibration phase, and one or more test stimuli during an emotional testing phase. For example, various types of stimuli may be retrieved from one or more of the calibration database 172 and/or the stimuli database 174, and presented to the subject via the display device 142, the speaker 144, and/or other output devices 148. In one implementation, the calibration database 172 and the stimuli database 174 may be included in a common stimuli database. The stimuli presentation module may also be or include an aroma synthesizer to generate aromas as test stimuli. Thus the stimuli, in various forms, may be stored or generated in real-time. In which case, the conditioning stimuli may be aroma based (or aroma-neutral, such as unscented or fresh air).

According to one implementation of the invention, the data collection module 156 may collect various forms of eye data, physiological data, and/or other data from the subject during each of the calibration phase, the conditioning phase, and the emotional testing phase. The data that the data collection module 156 collects may subsequently be stored in the collected data database 176.

According to one implementation of the invention, the data analysis module 158 may analyze the collected data (e.g. eye data and/or other data) in the collected data database 176. For example, the data analysis module 158 may analyze the data in the collected data database 176 to determine patterns and variations in gaze data, eye movement, pupil diameter, pupil size, blink rate, or otherwise for various subjects. Moreover, the data analysis module 158 may analyze the eye data in view of stimuli presented at different light intensities to determine scaling factors or criteria to normalize subsequent analysis that occurs during emotional testing of the subjects. As a result, the data analysis module 158 can determine an emotional impact of various stimuli based on the analysis of the eye data and other information in the collected data database 176. The results that data analysis module 158 produces may be directed for storage in the analysis results database 178.

FIG. 2 illustrates an exemplary method 200 for performing calibration of one or more subjects during a calibration phase, prior to conducting emotional testing of the subjects. The operations to be described in further detail herein may be accomplished using one or more of the components of the system described in greater detail above and, in some implementations, various of the operations may be performed in different sequences, in other orders, simultaneously, or various other operations may be performed along with some or all of the operations illustrated in FIG. 2. Accordingly, the description of the operations presented herein should be regarded as exemplary only.

In an operation 202, a subject may be positioned in front of one or more output devices, at least one of which includes an eye-tracking device (e.g., sitting, standing, or otherwise). The output devices may be used to present various calibration stimuli to the subject, while the eye-tracking device may collect eye-related information from the subject for calibration.

Gaze calibration may then be performed in an operation 204. In particular, the gaze calibration operation 204 may include instructing the subject to track, with his or her eyes, a moving visual indicator displayed on a display device. The eye-tracking device may therefore track the subject's eye movement to determine where on the display device the subject looks. The location where the subject looks may be defined as x, y, z and/or other co-ordinates. As such, the gaze calibration operation 204 may establish a frame of reference for the subject's gaze pattern (e.g., an eye movement pattern).

In a decisional operation 206, the gaze data or other data collected via the eye-tracking device during the gaze calibration operation 204 may be analyzed to determine whether the gaze data is valid. For example, the gaze data may be rendered invalid when analysis of the gaze data indicates that the subject was not looking at the display device or a given location or sequence of locations on the display device (e.g., corresponding to the location of the moving visual indicator). When decisional operation 206 determines that the gaze data is invalid, gaze calibration operation 204 may be repeated until valid gaze data can be obtained. In one implementation, repeating the gaze calibration operation 204 may include instructing the subject to re-position themselves, as in operation 202, prior to instructed the subject to again track the movement of the visual indicator on the display device in operation 204. In one implementation, when operation 206 determines that the gaze data is invalid, or when invalid gaze data is collected a predetermined number of times, the calibration may be terminated for the subject.

When decisional operation 206 does determine the gaze data to be valid, a pupil variation calibration may be performed in an operation 208. The pupil variation calibration may include presenting the subject with a predetermined sequence of one or more calibration stimuli having predetermined light intensity values or emotional criteria (e.g., neutral and/or other criteria of a stimulus). For example, the pupil variation calibration may present emotionally neutral stimuli having different light intensities (e.g., zero intensity, intermediate intensity, full intensity) via the display device to determine the subject's pupil diameter and pupil response to different light intensities. In one example, the predetermined sequence may include a zero intensity or black stimulus, followed by an intermediate intensity or gray stimulus. Then, another zero intensity or black stimulus may be presented followed by another intermediate intensity or gray stimulus. Thereafter, a full intensity or white stimulus may be presented.

The eye-tracking device may track and/or measure various eye properties of the subjects (e.g., pupil size, pupil dilation, blink rate, and/or other properties) at the different light intensities. Additionally, the eye-tracking device may sample the eye properties of the subjects at one or more rates that can enable the system to accurately measure the values for the eye properties. For example, the eye-tracking device may establish an average pupil diameter by taking a maximum, minimum, or average pupil diameter when the zero intensity stimuli were presented and averaging that pupil diameter with a maximum, minimum, or average pupil diameter when one or more of the intermediate or full intensity stimuli were presented. Thus, using the tracked data, variations in the subject's pupil diameter at different light intensities may be determined, and this data may subsequently be used to calibrate and normalize the subject's response to different test stimuli during emotional testing.

In an operation 210, an emotional baseline calibration may be performed. For example, one or more stimuli having a presumptively desired emotional impact (e.g. one or more emotionally neutral stimuli) may be presented to the subject via the display device or another output device. Eye properties or other sensory characteristics may be measured to determine an emotional state of the subject (e.g., blink rate, pupil size, eye movement, heart rate, pulse rate, etc.). Thereafter, a decisional operation 212 may include analyzing the eye properties or other sensory characteristics measured in operation 210 to determine whether the emotional state of the subject matches a desired emotional state. For example, the desired emotional state may generally include a neutral emotional state, although it will be apparent that other emotional states may be used as the emotional baseline, depending on the particular purpose of the emotional testing to follow. When the decisional operation 212 determines that the subject is not in the desired emotional state, the emotional baseline calibration operation 210 may be repeated until the blink rate pattern, pupil response, saccadic movements, heart rate, and/or other eye properties or sensory characteristics demonstrate that the subject has reached the desired emotional state, whereby emotional testing of the subject may commence in an operation 214.

FIG. 3 illustrates an exemplary method 300 for performing calibration of one or more subjects during a conditioning phase, which may occur while conducting emotional testing of the subjects. The operations to be described in further detail herein may be accomplished using one or more of the components of the system described in greater detail above and, in some implementations, various of the operations may be performed in different sequences, in other orders, simultaneously, or various other operations may be performed along with some or all of the operations illustrated in FIG. 3. Accordingly, the description of the operations presented herein should be regarded as exemplary only.

In one implementation, the conditioning phase may include presenting one or more conditioning stimuli to a subject prior to, in between, or among test stimuli presented to the subject. The conditioning stimuli may include one or more "interslides" having predetermined characteristics, which may be presented to the subject during various phases of emotional testing. As such, where emotional testing includes presenting one or more test stimuli slides to a subject, the interslide conditioning stimuli may include one or more slides having a primary purpose not of emotional response testing, but of conditioning the subject prior to those stimuli on which the emotional testing will focus.

For example, in an operation 302, the conditioning stimuli may include a fixation indicator presented to the subject at a predetermined location on a display device (e.g., at or near the center of the display device). The fixation indicator may include any suitable stimulus (e.g., a visual stimulus) to draw the subject's attention thereto. The fixation indicator may generally fix the subject's gaze at the predetermined location on the display device to condition or otherwise normalize the subject for one or more subsequent test stimuli. For example, the fixation indicator may be presented to establish an emotionally neutral gaze condition in the subject. In one implementation, operation 302 may include determining whether the subject's gaze has been suitably fixed based on a prior calibration of the subject's gaze (e.g., as determined during the aforementioned calibration process).

In another example, in an operation 304, the conditioning stimuli may include one or more emotionally neutral conditioning stimuli. The emotionally neutral interslides may increase the accuracy of eye data collected during emotional testing because the emotionally neutral interslides serve to bring the subject's emotional state back to a neutral state after having been exposed to test stimuli that can include strong emotional content.

For example, the interslide stimuli may have a predetermined light intensity, which may be based on a light intensity of a visual test stimulus subsequently presented in an operation 306. The interslide stimuli may have the same overall light intensity as the actual test stimulus presented in operation 306 (e.g., by scrambling pixels of the test pixels to create a distinct image having the same overall light intensity). As a result, the interslide stimuli presented in operation 304 may condition the subject's eyes to the light intensity of the test stimulus presented in operation 306. Therefore, when subsequently measuring various forms of eye data in an operation 308 (e.g., blink rate, pupil response, eye movement, etc.), any measured ocular response can be attributed primarily to the subject's emotional response to the test stimulus, rather than a change in light intensity.

In an operation 310, a determination may be made as to whether to present one or more further test stimuli to the subject. If further test stimuli are to be presented, the emotional testing of the subject may be continued, for example, by presenting a gaze fixation stimuli (e.g., operation 302) and/or emotionally neutral interslide conditioning stimuli (e.g., operation 304). After again presenting one or more of the conditioning stimuli, the further test stimuli may be presented and the subject's emotional response thereto measured (e.g., operations 306-308). However, it will be apparent that, in various implementations, one or more of operations 306 and 308 may be repeated without presenting the interslide conditioning stimuli.

One way in which the calibration data may be used is to determine a dynamic range of pupil dilation for each subject so that actual pupil dilation during testing can be normalized (using various known normalization techniques).

Aspects and implementations may be described as including a particular feature, structure, or characteristic, but every aspect or implementation may not necessarily include the particular feature, structure, or characteristic. Further, when a particular feature, structure, or characteristic has been described in connection with an aspect or implementation, it will be understood that such feature, structure, or characteristic may be included in connection with other aspects or implementations, whether or not explicitly described. Thus, various changes and modifications may be made to the preceding description without departing from the scope or spirit of the invention, and the specification and drawings should therefore be regarded as exemplary only, and the scope of the invention determined solely by the appended claims.

What is claimed is:

1. A computer-implemented method of measuring eye data of a subject during emotional testing, the method being implemented by a computer executing one or more applications, the method comprising:

obtaining, by the computer, a test stimulus;

obtaining, by the computer, a conditioning stimulus, the conditioning stimulus comprising scrambled pixels of the test stimulus;

causing, by the computer, the conditioning stimulus to be presented to a subject via a display device operatively coupled to the computer;

causing, by the computer, the test stimulus to be presented to the subject via the display device;

receiving, by the computer, from an eye-tracking device operatively coupled to the computer, eye data collected from the subject by the eye-tracking device while the subject viewed the test stimulus; and processing, by the computer, the collected eye data to determine the subject's emotional response to the test stimulus.

2. The method of claim 1, further comprising:
causing, by the computer, at least one stimulus to be presented to the subject, via the display device, prior to the conditioning stimulus, to induce a desired emotional state in the subject.

3. The method of claim 1, further comprising:
determining and recording, by the computer, an emotional baseline level of the subject prior to causing the conditioning stimulus to be presented to the subject.

4. The method of claim 1, wherein the conditioning stimulus has a same overall light intensity as the test stimulus, such that any ocular response to the test stimulus is based primarily upon the subject's emotional response to the test stimulus as opposed to a change in light intensity between the conditioning stimulus and the test stimulus.

5. The method of claim 1, further comprising:
causing, by the computer, a visual stimulus to be presented to the subject, via the display device, prior to presenting the conditioning stimulus to the subject, wherein the visual stimulus includes a fixation indicator for fixing the subject's gaze at a predetermined location.

6. The method of claim 1, wherein the collected eye data includes pupil data.

7. The method of claim 1, wherein the collected eye data includes blink data.

8. The method of claim 1, wherein the collected eye data includes gaze data.

9. The method of claim 1, wherein the eye-tracking device is integrated with the display device.

10. A system for measuring eye data of a subject during emotional testing, the system comprising:
a computer programmed to execute one or more applications that, when executed, cause the computer to:
obtain a test stimulus;
obtain a conditioning stimulus, the conditioning stimulus comprising scrambled pixels of the test stimulus;
cause the conditioning stimulus to be presented to a subject via a display device operatively connected to the computer;
cause the test stimulus to be presented to the subject via the display device;
receive, from an eye-tracking device operatively coupled to the computer, eye data collected from the subject by the eye-tracking device while the subject viewed the test stimulus; and
process the collected eye data to determine the subject's emotional response to the test stimulus.

11. The system of claim 10, wherein the computer is further caused to:
induce a desired emotional state in the subject by causing at least one stimulus to be presented to the subject, via the display device, prior to the conditioning stimulus.

12. The system of claim 10, wherein the computer is further caused to:
determine and record an emotional baseline level of the subject prior to causing the conditioning stimulus to be presented to the subject.

13. The system of claim 10, wherein the conditioning stimulus has a same overall light intensity as the test stimulus, such that any ocular response to the test stimulus is based primarily upon the subject's emotional response to the test stimulus as opposed to a change in light intensity between the conditioning stimulus and the test stimulus.

14. The system of claim 10, wherein the computer is further caused to:
present to the subject, via the display device, a visual stimulus prior to the conditioning stimulus, wherein the visual stimulus includes a fixation indicator for fixing the subject's gaze at a predetermined location.

15. The system of claim 10, wherein the collected eye data includes pupil data.

16. The system of claim 10, wherein the collected eye data includes blink data.

17. The system of claim 10, wherein the collected eye data includes gaze data.

18. The system of claim 10, wherein the eye-tracking device is integrated with the display device.

19. A computer program product to measure eye data of a subject during emotional testing, the computer program product comprising:
one or more tangible, non-transitory computer-readable storage devices;
program instructions, stored on at least one of the one or more tangible, non-transitory computer-readable tangible storage devices that, when executed, cause a computer to:
obtain a test stimulus;
obtain a conditioning stimulus, the conditioning stimulus comprising scrambled pixels of the test stimulus;
cause the conditioning stimulus to be presented to a subject via a display device operatively connected to the computer;
cause the test stimulus to be presented to the subject via the display device;
receive, from an eye-tracking device operatively coupled to the computer, eye data collected from the subject by the eye-tracking device while the subject viewed the test stimulus; and
process the collected eye data to determine the subject's emotional response to the test stimulus.

* * * * *